United States Patent [19]
Ploner

[11] 3,970,592
[45] July 20, 1976

[54] UNSATURATED HYDROCARBONS AND PROCESS FOR MAKING SAME
[75] Inventor: Klaus-Jürgen Ploner, Essen-Werden, Germany
[73] Assignee: Givaudan Corporation, Clifton, N.J.
[22] Filed: Jan. 22, 1975
[21] Appl. No.: 543,200

[30] Foreign Application Priority Data
Nov. 13, 1974 Switzerland............... 1259/74

[52] U.S. Cl................. 252/522; 260/666 B; 260/675.5; 260/677 R; 260/680 B; 260/683.2
[51] Int. Cl.².............. A61K 7/46; C11B 9/00; C07C 11/00
[58] Field of Search......... 260/666 B, 677 R, 680 B, 260/683 R, 683.2, 675.5; 252/522

[56] References Cited
UNITED STATES PATENTS

| | | | |
|---|---|---|---|
| 3,522,321 | 7/1970 | DeYoung | 260/666 B |
| 3,541,177 | 11/1970 | Hagihara et al. | 260/680 B |
| 3,691,249 | 9/1972 | DeYoung | 260/666 B |
| 3,714,284 | 1/1973 | Symon | 260/677 R |
| 3,732,328 | 5/1973 | Wright | 260/680 B |

OTHER PUBLICATIONS

Egloff, Physical Constants of Hydrocarbons, vol. V, (1953) pp. 462–467 (cf. Chem. Abs., 41, 3039e, 1947).
Chem. Abs., 78, 123978t 1973, Miyake et al.
Chem. Abs. 77, 47925k, (1972) Gaasbeek et al.

*Primary Examiner*—C. Davis
*Attorney, Agent, or Firm*—Thomas Cifelli, Jr.

[57] ABSTRACT

New unsaturated hydrocarbons, process for making same and odorant compositions containing same.
The preferred hydrocarbon is 2,7-dimethyl-1,4,6-octatriene. Perfumes, perfumed products such as soaps and cosmetic products are among the products in which the novel hydrocarbons may be used.

2 Claims, No Drawings

UNSATURATED HYDROCARBONS AND PROCESS FOR MAKING SAME

FIELD OF THE INVENTION

This invention relates to novel unsaturated hydrocarbons and odorant compositions containing them.

SUMMARY OF THE INVENTION

The unsaturated hydrocarbons provided by the present invention have the following general formula

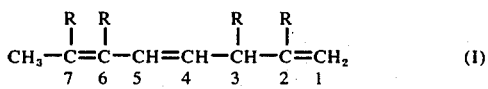

in which each R independently represents a hydrogen atom or a lower alkyl or lower alkenyl group with the proviso that not more than two R's represent hydrogen atoms and the R's at $C^2$ and $C^7$ do not simultaneously represent hydrogen atoms.

According to the process provided by the present invention, the unsaturated hydrocarbons of formula I hereinbefore are manufactured by treating a compound of the general formula

or a mixture of two or more compounds of formula II, or a compound of the general formula

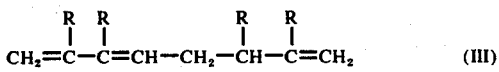

whereby the R's in the compounds of formulae II and III are so chosen that the R's in the product of formula I obtained have the meanings given above,
with palladium salts and/or coordinated palladium complexes in the presence of an acid catalyst.

The Unsaturated hydrocarbons of formula I are novel. They can be used as odorants or an intermediates for the manufacture of odorants (terpene analogues). In the latter instance, the customary techniques in terpene chemistry can be used for the manufacture of alcohols, esters, ethers and the like.

DESCRIPTION OF THE PREFERRED EMBODIMENTS

The term "lower" as used in this specification in connection with alkyl and alkenyl groups means that such groups contain up to 7 carbon atoms. Examples of lower alkyl groups are methyl, ethyl, propyl and butyl groups and isomers of the latter two groups. A preferred lower alkenyl group is 4-methylpenten-3-yl.

Examples of starting materials of formula II are isoprene, butadiene, 2,3-dimethyl-1,3-butadiene, 2-ethylbutadiene and myrcene. Isoprene and myrcene are preferred.

Examples of starting materials of formula III are 2,7-dimethyl-1,3,7-octatriene, 11-methyl-7-methylene-1,3,10-dodecatriene, 2,11-dimethyl-7-methylene-1,3,10-dodecatriene and 2,3,6,7-tetramethyl-1,3,7-octatriene.

Examples of palladium salts which can be used in the process provided by the present invention are palladium (II) salts such as Pd (II) nitrate, chloride, bromide and sulphate, Pd (II) alkanoates such as Pd (II) acetate, butyrate and hexanoate, $Na_2PdCl_4$, $K_2PdCl_4$, Pd (II) acetylacetonate, Pd (II) cycloalkanecarboxylates such as Pd (II) cyclohexanecarboxylate, Pd (II) arylcarboxylates such as Pd (II) benzoate and monomethylphthalate and palladium (IV) salts such as $K_2PdCl_6$, $K_2PdBr_6$, $(NH_3)_2PdCl_4$ and $(pyridine)_2PdCl_4$.

The coordinated palladium complexes used in the process of the present invention can contain, for example, ligands such as trialkylphosphines (e.g. tricyclohexylphosphine or tributylphosphine), triarylphosphines (e.g. triphenylphosphine), trialkylphosphites (e.g. triethylphosphite) and triarylphosphites (e.g. triphenylphosphite). As ligands, there can also be used phosphorus compounds in which the phosphorus is bonded not only to oxygen but also to caarbon (e.g. phenyl-di-n-butoxyphosphine). Palladium-olefin complexes or complexes with alkyl- and aryl-nitriles may also be used.

Examples of such coordinated palladium complexes are bis(triphenylphosphine)Pd (II) chloride, nitrate, carbonate or acetate, bis(dimethylphenylphosphine)-palladium (II) chloride, bis(trinaphthylphosphine)palladium (II) chloride, [1,2-(bis-diphenylphosphine)ethane]palladium (II) chloride, bis(trioctylphosphine)-palladium (II) nitrate, tetrakis(triphenylphosphine)palladium (O), tetrakis(dimethylphenylphosphine)palladium (O), tetrakis(tri-p-methoxyphosphine)palladium (O), tetrakis(diphenyl-p-chlorophenylphosphine)palladium (O), tetrakis(trinaphthylphosphine)-palladium (O), bis(p-methoxyphenyl)palladium (II) acetate, bis(triphenylphosphine)Pd. maleic acid anhydride, bis(triphenylphosphine)Pd.p-benzoquinone, bis(trioctylphosphite)palladium (II) nitrate, tetrakis(-triphenylphosphite)palladium (O), bis(triphenylphosphite)palladium (II) chloride, 1,5-cyclooctadienepalladium (II) chloride, $\pi$-allylpalladium acetate, endodicyclopentadiene-palladium (II) bromide, bis(Propionitrile)palladium (II) cyanide and bis(benzonitrile)-palladium (II) chloride.

The coordinated palladium complexes can also be prepared in situ in the mixture in which the treatment is carried out. In certain cases it is advantageous to add an excess of the ligands contained in the complex to the mixture. The amount of the ligands added is not critical, but is advantageously lies between 0 and 20 mol based on 1 mol of palladium catalyst. The amount of catalyst added is not critical, but 0.01 to 10% of catalyst based on the diene is preferably used.

Especially suitable acid catalysts are mineral acids such as sulphuric acid or, particularly, phosphoric acid, carboxylic acids (e.g. alkanecarboxylic acids such as acetic acid or trifluoroacetic acid), oxalic acid, p-toluenesulphonic acid etc. As the acid catalyst there can also be used salts such as potassium sulphate or so-called Lewis acids such as boron trichloride, boron trifluoride or zinc chloride. The amount of acid catalyst used can vary within a wide range; for example 0.01–100 mol of acid catalyst can be used per mole of palladium compound. However, the amount of acid catalyst depends to a certain extent on the strength of the acid. In the case of a mineral acid such as phosphoric acid about 0.01 to 10 mol is preferred and in the case of a carboxylic acid such as acetic acid about 1 to 100 mol is preferred. The weaker the acid, the greater amount is used and vice versa.

The present process can be carried out in the presence or absence of a solvent. As solvents, there are preferably used those which are inert towards the starting materials and unsaturated hydrocarbons of formula I and in which the catalyst is at least partly soluble. Examples of such solvents are linear and cyclic ethers (e.g. diethyl ether, tetrahydrofuran or dioxane), alcohols (e.g. methanol, ethanol or propanol), ketones (e.g. acetone), acid amides (e.g. dimethylformamide), nitriles (e.g. acetonitrile), pyridine and homologues thereof, aliphatic hydrocarbons which may be chlorinated (e.g. hexane or dichloroethane), aromatic hydrocarbons which may be chlorinated (e.g. benzene, toluene or chlorobenzene), olefins, esters, sulphones and phosphoric acid amides.

When the present process is carried out in the absence of a solvent, a catalyst which is at least partly soluble in the mixture is chosen.

The present process can be carried out, for example, at a temperature between 60° and 150°C, with a temperature between 80° and 125°C being preferred. The treatment can be carried out in a pressure vessel under its own pressure or at an elevated pressure or at atmospheric pressure.

In order to achieve optimal yields, the course of the process is expediently followed analytically by taking samples, for example gas chromatographically.

The unsaturated hydrocarbons of formula I are novel. They can be used as odorants or as intermediates for the manufacture of odorants (terpene analogues). In the latter instance, the customary techniques in terpene chemistry can be used for the manufacture of alcohols, esters, ethers and the like.

The unsaturated hydrocarbons of formula I can be used, for example, as odorants in perfumery for the manufacture of odorant compositions such as perfumes or for perfuming products of all types such as soaps (for which they are especially suitable because of their stability), washing agents, detergents, aerosols or cosmetic product such as ointments, face milk, make-up, bath salts etc.

The concentration of the unsaturated hydrocarbons of formula I in odorant compositions or perfumed products can vary within wide limits depending on the intended use. For example, the concentration can lie between about 1 wt.% and about 10 wt.% in perfume bases. The preferred concentrations in the case of odorant compositions lie in the range of about 0.1 wt.% to about 20 wt.%. The concentration of the perfume base can amount, for example, to about 0.8–2 wt.% in soaps and to 0.1–0.3 wt.% in washing agents.

The preferred compounds of formula I are the 2,7-di(lower alkyl)-1,4,6-octatrienes. 2,7-Dimethyl-1,4,6-octatriene as a typical, preferred representative of this subclass is an especially interesting compound (from the organoleptic point of view and as an intermediate). Its odour is terepene-like, green, fatty and soapy. This compound is very well suited for use not only in compositions of the lavender type, but also in flowery compositions such as lilac, gardenia, hyacinth etc. The addition of this compound to such compositions bestows a radiant fullness to the compositions.

Generally, it can be said that the compounds of formula I are from the organoleptic point of view particularly interesting because their odour is natural, not "solvent-like" as is the odour of known compounds which are structurally related to the compounds of formula I.

It will accordingly be understood that the invention also includes within its scope (a) an odorant composition which contains as an essential odour-imparting ingredient an unsaturated hydrocarbon of formula I hereinbefore and (b) a method of imparting an odour to materials by applying thereto or incorporating therein an odour-imparting amount of an unsaturated hydrocarbon of formula I hereinbefore.

The following Examples illustrate the process provided by the present invention:

EXAMPLE 1

50 ml of distilled isoprene, 1 kg of dioxane, 5 g (16.5 mmol) of palladium acetylacetonate, 23.1 g (82.5 mmol) of tricyclohexylphosphine and 1.9 g (16.5 mmol) of 85% phosphoric acid in a four-necked flask are held under reflux under an argon atmosphere until the internal temperature exceeds 90°C. 1 kg of isoprene is then added dropwise at an oil-bath temperature of 120°C in such a manner that the internal temperature does not fall below 88°C (ca 30 ml/hour) but remains in the range of 90°–95°C. After 50 hours, the isoprene addition is terminated, the product now consisting essentially of 2,7-dimethyl-1,3,7-octatriene. The mixture is left to react for a further 40 hours, the internal temperature rising to 105°–108°C. The dioxane is now removed on a rotary evaporator at 40°C/20 mm Hg. The black-coloured residual oil is steam-distilled, 780 g of distillate being obtained. The residue (trimers and polymers) amounts to 215 g. By fractional distillation of the oil on a Raschig-ring column at 63°C/10 mm Hg, there are obtained 550 g of 2,7-dimethyl-1,4,6-octatriene; $n_D^{20}$ =1.4885. Odour: fatty, green, soapy, terpene-like.

EXAMPLE 2

17 g of isoprene, 25 g of dioxane, 0.3 g of palladium acetylacetonate, 1.4 g of tricyclohexylphosphine and 0.14 g of boron trifluoride etherate are heated for 10 hours at 100°C in an autoclave under an argon atmosphere. After cooling, the mixture is completely distilled off from the catalyst at 40°C/0.1 mm Hg and the solvent and excess isoprene are removed at 10 mm Hg. There are obtained 14.3 g of a colourless oil which consists of 58% 2,7-dimethyl-1,4,6-octatriene according to gas chromatographic analysis.

$^1$H—NMR: $\tau$ = 3.70 (1H, 2d, J = 10 + 15); 4.17 (1H, d, J = 10);
4.53 (1H, 2d, J = 6.5 + 15); 5.29 (2H, s);
7.21 (2H, d, J = 6.5); 8.28 (9H, s).

EXAMPLE 3

54 g of isoprene are reacted with 27 g of myrcene at 100°C for 30 hours in a manner analogous to that described in Example 1. The mixture can be separated by distillation into its C$_{10}$ and C$_{15}$ constituents. The C$_{10}$ constituent (27.0 g; boiling point 38°–68°C/10 mm Hg) consists of 62.7% 2,7-dimethyl-1,4,6-octatriene. The C$_{15}$ constituent (20.4 g; boiling point 66°–69°C/0.1 mm Hg) comprises 44% of the two codimers of isoprene and myrcene, 2,11-dimethyl-7-methylene-2,4,10-dodecatriene and 2,7,11-trimethyl-1,4,6,10-dodecatetraene, in the ratio 1:3. A small amount of the codimer mixture is separated by prepartive gas chromatography. There is obtained the following $^1$H—NMR spectrum:

τ = 3.5–5.2 (4H, m); 5.3 (2H, s); 7.25 (2H, d, J = 7); 7.97 (4H, m); 8.3 (10H, s); 8.4 (2H, s).

EXAMPLE 4

A mixture of 20.5 g of dimethylbutadiene, 25 g of dioxane, 0.225 g of palladium acetate, 1.85 g of trioctylphosphine and 0.14 g of boron trifluoride etherate are heated at 100°C for 24 hours in a 100 ml autoclave under an argon atmosphere. The mixture is worked-up in a manner analogous to that described in Example 2 and there are obtained 20.1 g of a crude product which consists of 40.6% 2,3,6,7-tetramethyl-1,4,6-octatriene according to gas chromatographic analysis. By means of a 1 meter spinning-band column the product can be separated in pure form; boiling point 89°C/10 mm Hg; $n_D^{20}$ = 1.4973.

$^1$H—NMR: τ = 3.45 (1H, d, J = 16); 4.45 (1H, 2d, J = 8 + 16);
5.23 (2H, s); 7.10 (1H, m);
8.22 (9H, s); 8.30 (3H, s);
8.90 (3H, d, J = 8).

EXAMPLE 5

10 g of 2,7-dimethyl-1,3,7-octatriene are kept at reflux temperature under argon atmosphere for 24 hours together with 25 ml of isopropanol and 0.384 g of (PhCN)$_2$PdCl$_2$ and 0,1 g of H$_3$PO$_4$. After this period 75.3% of 2,7-dimethyl-1,4,6-octatriene have been formed (GC-analysis).

EXAMPLE 6

10 g of dimethyl-1,3,7-octatriene are kept under argon atmosphere for 36 hours with 0,303 g palladium acetylacetonate, 1,4 g of tricyclohexylphosphine and 0,1 g of H$_3$Po$_4$. After this period, 80.3% of 2,7-dimethyl-1,4,6-octatriene have been formed (GC-analysis).

Example A

| Lavender composition | Parts by weight |
|---|---|
| 2,7-Dimethyl-1,4,6-octatriene | 40 |
| Resinoid Castoreum | 5 |
| Clove oil Zanzibar | 5 |
| Patchouli oil 10% in ethyl phthalate | 10 |
| Geranium oil Bourbon | 10 |
| Sandalwood oil East Indian | 10 |
| Oil of thyme white | 10 |
| Orange oil Californian | 20 |
| Rosemary oil Spanish | 20 |
| Musk ketone | 20 |
| Musk infusion 3% in ethanol | 30 |
| Balsam tolu resinoid 50% in ethyl phthalate | 30 |
| Spike oil Spanish | 30 |
| Neroli oil synthetic | 20 |
| Civet infusion 3% in ethanol | 40 |
| Bergamot oil Reggio | 200 |
| Lavender oil French | 500 |
| | 1000 |

What is claimed is:
1. 2,7-Dimethyl-1,4,6-octatriene.
2. An odorant composition which contains an olfactorilyeffective amount of 2,7-dimethyl-1,4,6-octatriene and at least one other olfactory agent.